United States Patent
Bosin et al.

(10) Patent No.: US 9,717,444 B2
(45) Date of Patent: Aug. 1, 2017

(54) OPTICAL POLARIZATION SHIFT MEASURING SYSTEM

(71) Applicants: Mark Bosin, Kharkiv (UA); Seva Brodsky, Jerusalem (IL); Leonid Pasichnyk, Kharkiv (UA)

(72) Inventors: Mark Bosin, Kharkiv (UA); Seva Brodsky, Jerusalem (IL); Leonid Pasichnyk, Kharkiv (UA)

( * ) Notice: Subject to any disclaimer, the term of this patent is extended or adjusted under 35 U.S.C. 154(b) by 377 days.

(21) Appl. No.: 13/954,627

(22) Filed: Jul. 30, 2013

(65) Prior Publication Data

US 2014/0036254 A1   Feb. 6, 2014

Related U.S. Application Data

(60) Provisional application No. 61/679,019, filed on Aug. 2, 2012.

(51) Int. Cl.
| | |
|---|---|
| *G01N 21/21* | (2006.01) |
| *A61B 5/145* | (2006.01) |
| *A61B 5/1455* | (2006.01) |
| *G01N 21/359* | (2014.01) |

(52) U.S. Cl.
CPC ........ *A61B 5/14532* (2013.01); *A61B 5/1455* (2013.01); *A61B 5/14558* (2013.01); *G01N 21/21* (2013.01); *A61B 2560/0223* (2013.01); *A61B 2562/0238* (2013.01); *G01N 21/359* (2013.01)

(58) Field of Classification Search
CPC . A61B 5/14558; A61B 5/14532; G01N 21/21
USPC .................................................. 600/319, 316
See application file for complete search history.

(56) References Cited

U.S. PATENT DOCUMENTS

| | | | |
|---|---|---|---|
| 4,901,728 | A | 2/1990 | Hutchison |
| 5,009,230 | A | 4/1991 | Hutchinson |
| 5,209,231 | A | 5/1993 | Cote et al. |
| 5,398,681 | A | 3/1995 | Kupershmidt |
| 5,448,992 | A | 9/1995 | Kupershmidt |
| 5,687,721 | A | 11/1997 | Kuhls |
| 5,703,364 | A | 12/1997 | Rosenthal |

(Continued)

OTHER PUBLICATIONS

Chi-Fuk So et al., Recent advances in noninvasive glucose monitoring; Medical Devices: Evidence and Research, 5: 45-52 (2012); pp. 47-48.

(Continued)

*Primary Examiner* — Yara B Green (57) ABSTRACT

A non-invasive device for measuring concentration levels of optically active substances, such as glucose, by determination of polarization plane turn angle in the infrared spectrum. Instant embodiments, measuring optical polarization shift, include a narrow-band optical source having a first linear polarizer; substantially illuminated by the source, a sample stage capable of temporarily immobilizing a sample; proximate to the sample stage and within a predetermined angular range with respect to the source illumination of the sample, a narrow-band optical detector capable of detecting polarization angles from the illuminated sample; and in conjunction with the source and the detector, a linear polarization angle comparator for comparing a polarization of the source with a polarization maxima region measured by the detector.

17 Claims, 4 Drawing Sheets

(56) References Cited

U.S. PATENT DOCUMENTS

| | | | |
|---|---|---|---|
| 5,788,632 A * | 8/1998 | Pezzaniti | G01N 21/21 356/368 |
| 5,871,442 A | 2/1999 | Madarasz et al. | |
| 6,070,093 A * | 5/2000 | Oosta | A61B 5/0095 356/39 |
| 6,236,870 B1 | 5/2001 | Madarasz et al. | |
| 6,246,893 B1 * | 6/2001 | Gobeli | A61B 5/14558 600/318 |
| 6,567,678 B1 | 5/2003 | Oosta et al. | |
| 6,594,510 B2 | 7/2003 | Madarasz et al. | |
| 7,239,902 B2 * | 7/2007 | Schmitt | A61B 5/0059 600/310 |
| 8,412,293 B2 | 4/2013 | Rule | |

OTHER PUBLICATIONS

John L. Smith, the Pursuit of Noninvasive Glucose: "Hunting the Deceitful Turkey"; 2nd Ed. (2011); pp. 35-42, 45-46, 49.

Andrea Tura et al., Non-invasive glucose monitoring: Assessment of technologies and devices according to quantitative criteria; Diabetes Research and Clinical Practice, 77: 16-40 (2007); pp. 19-20, 22.

David Cunningham et al., Ed., In Vivo Glucose Sensing (Chemical Analysis: A Series of Monographs on Analytical Chemisty and Its Applications); Wiley (2009); pp. 5, 217-218, 331-334, 343, 349, 357-359.

Valery V. Tuchin, Ed., Handbook of Optical Sensing of Glucose in Biological Fluids and Tissues; CRC Press (2009); 457-461, 487-490, 527-530, 534-536.

\* cited by examiner

OPTICAL POLARIZATION SHIFT MEASURING SYSTEM

CROSS-REFERENCE TO RELATED APPLICATIONS

This application claims the benefit under 35 USC §119(e) of U.S. Provisional Application No. 61/679,019 filed on Aug. 2, 2012 and titled "Non-invasive polarizing blood glucose level meter."

BRIEF DESCRIPTION OF THE DRAWINGS

The invention is explained in more detail with reference to the various exemplary embodiments shown in the drawings, wherein.

SUMMARY OF THE INVENTION

An objective of the present invention is to present a device for non-invasive measurement of the level (or concentration) of optically active substance or substances in a sample. Another objective is to present a device for such measurements in aqueous solutions. Yet another objective is to enable non-invasive measurement of glucose concentration in human blood. Further objective is to increase the accuracy of non-invasive measurement of glucose concentration in human blood. These objectives are achieved in several related alternative ways as described below and shown in the embodiments of FIGS. 2 through 8.

The present invention pertains, inter alia, to example devices for non-invasive measurement of concentration of glucose in human blood. When various such devices were being developed in the 1980s-90s, great hopes were placed on spectroscopic methods. This is due to the well-known fact that glucose is an optically active substance in the near-infrared region, forcing the angle of polarization of the infra-red (IR) light beam passing through it to turn. Polarization plane of the light beam turns as it passes through human tissue, such as the several layers within human skin (for example, the skin area between the thumb and the index finger, or through earlobe, fingertip, etc.), due to the presence of glucose in human tissue at relatively stable concentration levels.

The visible part of the light spectrum is typically not useful for such measurements, as the optical activity of glucose is considered negligible in that region. Therefore, efforts have been directed at creating glucometers that would allow conducting measurements in the near-IR part of the spectrum; specifically, with the wavelength exceeding 0.75 µm (micrometer or micron), where glucose's optical activity increases noticeably.

However, the main obstacle there has been high concentration of water, which strongly absorbs IR light, in human tissues. Nevertheless, water has three spectral "windows of transparency" above its freezing point in the following exemplary wavelength ranges: (a) up to 1.35 µm; (b) from 1.55 up to 1.85 µm; and (c) from 2.10 up to 2.30 µm. Characteristics for glucose peaks of absorption within the second and third intervals have previously been used for determination of glucose concentration in blood. It has been possible to measure a low concentration of glucose at a level of 100 mg/L (or 10 mg/dL) in a calibrated glucose solution.

Unfortunately, when testing on human subjects using live human tissue containing blood vessels, such as fingertips, earlobes, etc., things turned out to be a lot more complicated. Within the last decade, there have been a number of attempts to create non-invasive glucometers by determining the concentration of glucose in human blood using light polarization, but thus far nobody succeeded in utilizing that concept for creating a functional device. An essential shortcoming of such methods and devices has been the impossibility to accurately measure the turn angle of the polarization plane within a fingertip—or, for that matter, in any other part of the human body—since this angle is very small (measured in angular seconds or even fractions thereof, rather than in degrees); also, the corresponding change of the light beam intensity is too minute—so much so that existing modern electronics cannot measure it precisely. The measurement error constitutes about 30%, which is too large for medical purposes. There have also been other attempts to develop non-invasive devices using other phenomena, which have been described in technical literature previously, but all of them have been unsuccessful thus far, not resulting in any viable production devices that have made it to the marketplace.

The present invention comprises, inter alia, a new IR polarization mechanism with several novel and distinct features, which have not yet been described or employed by others to date, to the best of our knowledge. None of the reviewed prior art items disclosed either a method or an apparatus that could be considered essentially similar to those disclosed in the present invention. One of the major advantages of such a non-invasive glucometer would be its accurate measurements at the high end of blood glucose concentration (as well as throughout the range)—something that has been measured notoriously inaccurately (unlike for the low end) by the current finger-pricking method. Moreover, the present invention, being essentially a real-time device, enables the creation of practical devices for noninvasive real-time continuous glucose measurement and monitoring.

Various embodiments of the present invention relate to an optical polarization shift measuring system comprising: (A) a narrow-band optical source having a first linear polarizer; (B) substantially illuminated by the source, a sample stage capable of temporarily immobilizing an organic sample; (C) proximate to the sample stage and within a predetermined angular range with respect to the source illumination of the sample, a narrow-band optical detector capable of detecting polarization angles from the illuminated sample; and (D) in conjunction with the source and the detector, a linear polarization angle comparator for comparing a polarization of the source with a polarization maxima region measured by the detector. The reader should note that instant embodiments, herein also called a non-invasive polarizing blood glucose level meter, are merely exemplary and should not be viewed as limiting in any way, as there could be other embodiments employing the novel ideas presented herein.

According to some instant embodiments, the optical source is at least one substantially monochromatic near-infrared light source. Such source may comprise a laser, a laser diode, or a light-emitting diode (LED). At least one narrow bandwidth filter may be used in conjunction with the source. According to one embodiment, the optical source is a laser. Whether a single laser or multiple lasers are used as the optical source, or whether a spectrum-filtered broadband non-coherent light source is used as the optical source, variation embodiments of the instant invention particularly provide for glucose-measurement-relevant instantiations, wherein the optical source provides or includes illumination from about 0.75 μm to about 1.35 μm; or wherein the optical source provides or includes illumination from about 1.55 μm to about 1.85 μm; or wherein the optical source provides or includes illumination from about 2.10 μm to about 2.30 μm; or the like. Using multiple sources at different frequencies, including those within different water transparency windows, may increase measurement certainty and accuracy while decreasing its error.

Various instant embodiments relate to facile combinations, such as wherein the first linear polarizer is fixed and the detector includes a rotating front-end linear polarizer; or wherein the first linear polarizer is fixed and the detector includes a rapidly rotating front-end linear polarizer; or wherein the first linear polarizer is rotating and the detector includes a rapidly rotating front-end linear polarizer; or wherein the first linear polarizer is rotating and the detector includes a rotating front-end linear polarizer; or wherein the first linear polarizer is rotating and the detector includes a rapidly rotating front-end linear polarizer; or wherein the first linear polarizer is rapidly rotating and the detector includes a fixed front-end linear polarizer; or wherein the first linear polarizer is rapidly rotating and the detector includes a rotating front-end linear polarizer; or wherein the first linear polarizer is rapidly rotating and the detector includes a rapidly rotating front-end linear polarizer; or the like. Each of these combinations will allow detection of a slight shift of polarization angle, which occurs in the sample stage.

According to further instant invention variation embodiments, the sample stage is illuminated directly by the source; or the sample stage is illuminated by the source via optical fiber. Instant invention variation embodiments also relate to appurtenances of the sample stage such as including a cuvette or the like, so that the temporarily immobilized sample is a substantially sample-stage-size portion selected from the list: live human, live animal, vegetable, fruit, plant, tissue sample, and liquid sample; for example, a portion selected from the list: a finger, a toe, an earlobe, a roll of belly fat, a pinch of connective skin, a pinch of fatty skin, or the like.

According to other instant invention variation embodiments, the sample stage includes a plurality of optical pathways traversing illumination between the optical source and the detector. Furthermore, typically at least one of the optical pathways traversing the sample stage includes at least one optical element selected from the list: a concentrator, a lens, a collimator, a mirror, a reflector array, a prism, and a lenticular surface for projecting illumination from the source to the sample; or from the source to the detector; or from the source-illuminated sample into the detector.

Variation embodiments of the instant invention particularly provide for glucose-measurement-relevant instantiations wherein the detector includes a front-end optical bandwidth filter; and therewith the optical bandwidth filter allows light to pass through from about 0.75 μm to about 1.35 μm; or the optical bandwidth filter allows light to pass through from about 1.55 μm to about 1.85 μm; or the optical bandwidth filter allows light to pass through from about 2.10 μm to about 2.30 μm; or the like. Likewise, there are instant embodiments wherein illumination traversing the sample further traverses via an optical fiber to the detector.

Preferred embodiments of the instant invention further include external calibration of a sample with at least one light polarization-shifting substance in solution or in suspension in the sample; such as wherein the at least one light-polarization-shifting substance is glucose, or a form of sugar, or albumin, or ascorbate, or cholesterol, or a liquid crystal, or the like. Preferred embodiments of the present invention could be used to measure the presence and concentration of other optically active substances.

Typical instant embodiments also provide that the comparator includes an electronic block having at least one item selected from the list: a light detector, a processor, a display, an analog-to-digital transformation circuit (A/D converter), a communications interface, a synchronizer, a programmable logic interface, a statistical data collector, a statistical data analyzer, and a statistical data processor. Likewise, instant embodiments also provide that the polarization maxima region is substantially a zero-signal crossing.

Further embodiments of the present invention relate to a sample stage comprising a partially enclosed volume and a plurality of optical pathways through the volume, which are permitting traversing of predetermined illumination between an optical source and a detector. In this context, instant embodiments of the sample stage are further including at least one optical fiber to bring the illumination traversing a pathway of the plurality of pathways back into another pathway of the plurality of pathways; such as wherein the at least one optical fiber and the plurality of optical pathways through the volume together form at least one helictical pathway; or wherein the at least one optical fiber and the plurality of optical pathways through the volume together form at least one substantially sinusoidal pathway; or wherein the at least one optical fiber and the plurality of optical pathways through the volume together form at least one substantially poloidal pathway. Likewise, in this context, other instant embodiments of the sample stage further include at least one optical element selected from the list: a concentrator, a lens, a collimator, a mirror, a reflector array, a prism, and a lenticular surface for concentrating illumination over at least one pathway of the plurality of optical pathways through the volume; or are further comprising a low-noise optical signal amplifier. Preferably, the plurality of optical pathways through the volume is from about 4 to about 10 optical pathways, although other numbers of pathways may be used; since (to some extent) the greater the number of optical pathways, the greater the amplification or signal accuracy. Likewise, typically a pathway of the plurality of optical pathways through the volume includes not more than about a one-centimeter cross-section through the volume, although greater or lesser thickness could be used, given that the greater the thickness, the larger the turn angle of the plane of polarization, but, at the same time, the greater the attenuation of the light beam through the sample. It should be noted that embodiments of these sample stages also relate to specific-use embodiments herein called cut fiber optic cable examples. Other embodiments of the present invention may comprise mirrors, reflector arrays, prisms, or the like.

Embodiments of the present invention also relate to a method of optical polarization shift measuring comprising (A) providing a narrow-band optical source having a first linear polarizer; (B) therewith substantially illuminating a sample stage capable of temporarily immobilizing a sample; (C) proximate to the sample stage and within a predetermined angular range with respect to the source illumination of the sample, detecting polarization angles from the illuminated sample using a narrow-band optical detector; and (D) in conjunction with the source and the detector, comparing polarization of the source with polarization maxima region measured by the detector.

Likewise, other embodiments of the present invention relate to an article comprising a non-transitory tangible medium encoding computer-readable instructions that, when applied to one or more microprocessors, instruct one or more electronic components: (A) to illuminate a sample stage, having therein a temporarily immobilized sample, with a narrow-band optical source having a first linear polarizer; (B) to detect the illuminated sample using a narrow-band optical detector proximate to the sample stage and within a predetermined angular range with respect to the source illumination of the sample; and (C) to compare the polarization of the source with a polarization maxima region measured by the detector.

DETAILED DESCRIPTION OF THE PREFERRED EMBODIMENTS

Figure 1:
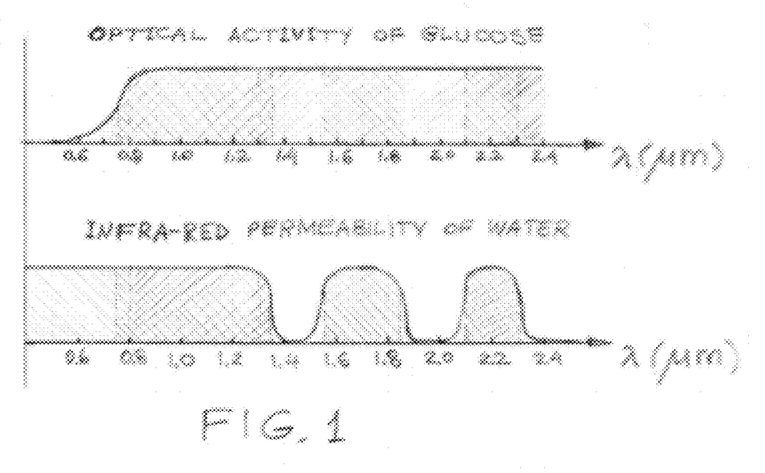
FIG. 1 is a graph of infra-red regions of optical activity of glucose and of optical permeability of water.

Referring to the drawings, particularly to FIG. 1, which shows an approximate sketch of a graph of optical activity of glucose placed above an approximate sketch of a graph of infra-red permeability of water, the three regions, in which the optical activity of glucose and infra-red water transparency intersect, can be seen as the three criss-crossed areas.

Figure 2:
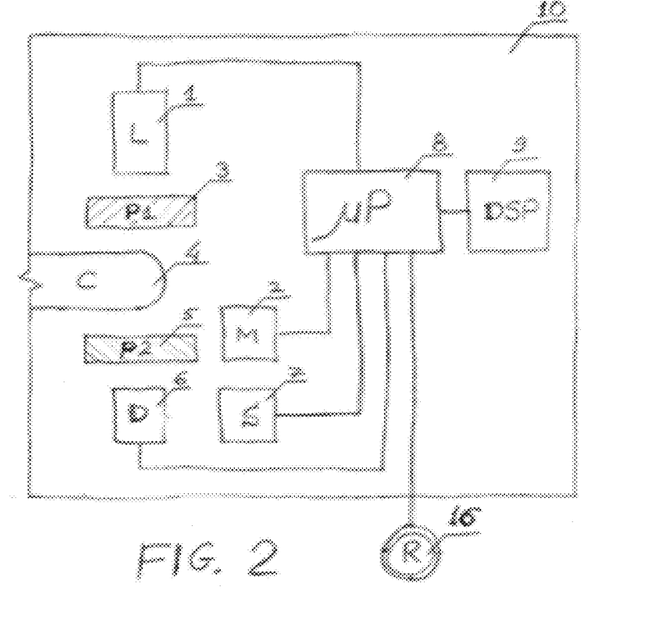
FIG. 2 is a schematic block diagram view of one embodiment of the invention, showing a rotational sampling mechanism for measuring the polarization plane turn angle.

Referring to the drawings, particularly to FIG. 2, which is a schematic block diagram view of one embodiment of the invention, showing a rotational sampling mechanism for measuring the polarization plane turn angle, the block diagram schematic discloses infrared laser 1, which sends a beam of IR light through stationary light beam polarizer 3. The flatly polarized light beam enters cuvette 4. Upon exiting from cuvette 4, the polarized IR light beam passes through a second, rotating polarizer 5. To have zero light intensity at detector 6, second polarizer 5 has to have its direction of linear polarization perpendicular to that of first polarizer 3. If cuvette 4 is empty, the beam will be completely absorbed in the second polarizer 5, and light detector 6 will detect no light at all. If cuvette 4 contains a live human body part (such as human fingertip, earlobe, etc.), this will force the plane of polarization of the polarized light beam to rotate slightly inside the human tissue by angle α, giving rise to a detected signal at light detector 6. Second polarizer 5 is mechanically connected to electric motor mechanism 2, which rotates polarizer 5 within the range of approximately 1,000-5,000 revolutions per minute. The light beam enters light detector 6, which is connected to piezoelectric synchronizer 7 that is connected to pulse sensor ring 16 worn by a person. Laser 1, motor mechanism 2, detector 6, and piezo synchronizer 7 are all controlled by electronic module 8, which contains a processor that also receives and processes the detected signal. Electronic module 8 then sends blood glucose concentration 9 and other relevant information to electronic display 9, which may be incorporated into electronic module 8. Most of the components of the device may be located within rigid housing 10.

Figure 3:
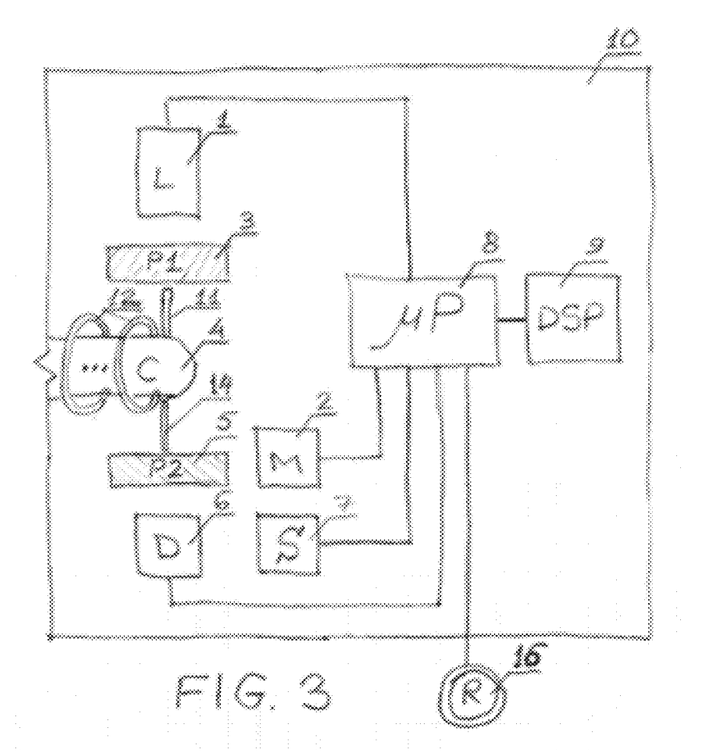
FIG. 3 is a schematic block diagram view of another embodiment of the invention, showing a fiber optic cable mechanism for measuring the polarization plane turn angle.

Referring to the drawings, particularly to FIG. 3, which is a schematic block diagram view of another embodiment of the invention, showing a fiber optic cable mechanism for measuring the polarization plane turn angle, the block diagram schematic discloses IR laser 1, which sends a beam of IR light through stationary light beam polarizer 3. The flatly polarized light beam is channeled through fiber optic cable 11 and enters cuvette 4. Fiber optic waveguides do not contribute significantly to depolarization, especially at short stretches. If cuvette 4 contains a live human body part (such as human fingertip, earlobe, etc.), this will force the plane of polarization of the polarized beam of IR light to rotate slightly inside the human tissue by angle α. Upon exiting from cuvette 4, the polarized and slightly rotated IR light beam passes through a fiber optic cable (helictical) spiral coil 12, which is cut into a number (say, up to 10) of tightly grouped near-circular sections (loops). The light exiting human tissue in cuvette 4 enters a section of spiral 12, travels through it, and is then channeled back into the tissue in cuvette 4, upon exiting which it is redirected back into the tissue through the next section of coil 12. This forces the polarized light beam to turn by angle α again and again, increasing the rotation angle of polarization plane by a multiple of α. This multiple is equal to the number of turns in the spiral plus one (N+1), since if there were no spiral coil, there would be just one turn of the polarization plane by angle α due to a single pass through the sample in cuvette 4. Upon exiting from cuvette 4, the IR light beam travels through fiber optic cable 14 and goes through second polarizer 5. Then the light beam enters detector 6, which is connected to piezoelectric synchronizer 7 that is connected to pulse sensor ring 16 worn by a person. Laser 1, motor 2 (in the automatic version of the device) for rotating second polarizer 5, detector 6, and piezo synchronizer 7 are all controlled by electronic module 8, which contains a processor that also receives and processes the detected signal. Electronic module 8 then sends blood glucose concentration φ and other relevant information to electronic display 9, which may be incorporated into electronic module 8. Most of the components of the device may be located within rigid housing 10.

Figure 4:
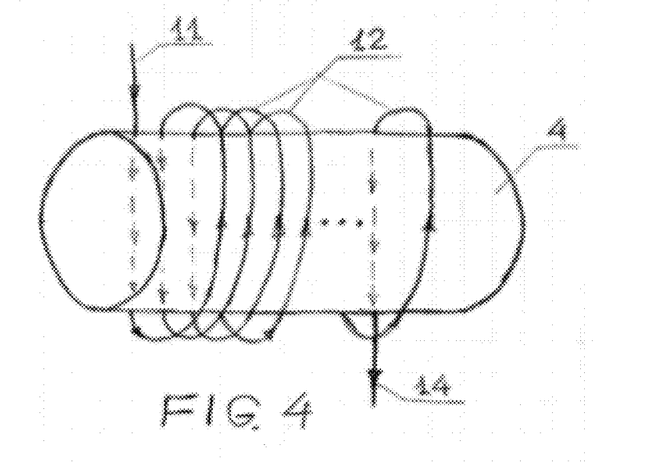
FIG. 4 is a schematic block diagram view of a cuvette with a single cut fiber optic cable coil on one side of the cuvette.

Referring to the drawings, particularly to FIG. 4, which shows a section of FIG. 3 in greater detail, namely, a schematic block diagram view of cuvette 4 with a single cut fiber optic cable coil 12 on one side of cuvette 4, it can be seen that after the light exits fiber optic cable 11 and goes through the sample in cuvette 4, it enters the first turn of coil 12, exiting it and going through the sample again and entering the second turn of coil 12, and so on, until it exits the last turn of coil 12, goes through the sample in cuvette 4 for the last time, and enters fiber optic cable 14, proceeding to second polarizer 5 shown in FIG. 3.

Figures 5, 6:
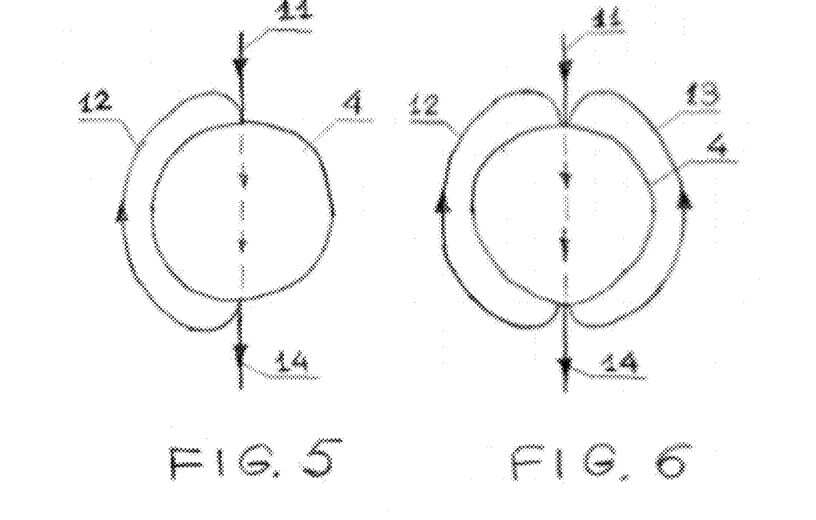
FIG. 5 is a schematic block diagram cross-sectional view of a cuvette with a single substantially helictical cut fiber optic cable coil aligned on one side of the cuvette.
FIG. 6 is a schematic block diagram cross-sectional view of a cuvette with a pair of substantially helictical cut fiber optic cable coils aligned on either side of the cuvette in another fiber optic cable coil embodiment of the invention.

Referring to the drawings, particularly to FIG. 5, which shows a cross-section of FIG. 4, that is, a schematic block diagram cross-sectional view of cuvette 4 with a single cut fiber optic cable coil on one side of cuvette 4, the approximate geometry seen in FIG. 5 corresponds to looking at cuvette 4 on FIG. 4 from the right side of FIG. 4.

Referring to the drawings, particularly to FIG. 6, which shows a schematic block diagram cross-sectional view of cuvette 4 in another embodiment of the invention, this embodiment, while essentially similar to the embodiment shown in FIGS. 3-5, differs in that it comprises a pair of cut fiber optic cable coils, 12 and 13, on either side of cuvette 4 rather than just one coil 12 shown in FIGS. 3-5. This different embodiment geometry can be seen in FIG. 6, which is similar to FIG. 5 in that we are looking at cuvette 4 from the right side of FIG. 4, except that the number of coils in FIG. 6 is two instead of one in FIG. 5. In the embodiment of FIG. 6, the light travels through the two coils, 12 and 13, in the following alternating manner: the light exits fiber optic cable 11 and goes through the sample in cuvette 4, entering the first turn of coil 12, exiting it and entering the first turn of coil 13. Upon exiting the first turn of coil 13, the light goes through the sample in cuvette 4, entering the second turn of coil 12, and so on, until it exits the last turn of coil 13, goes through the sample in cuvette 4 for the last time, and enters fiber optic cable 14, proceeding to second polarizer 5 shown in FIG. 3. This is not the only possible arrangement or order of the light passing through the turns of the two coils—there could be other configurations and other embodiments. This is merely one way of accomplishing the goal of making a more compact device. For example, in the embodiment shown in FIG. 6, the length of the coils and the number of turns in each coil could be reduced by a factor of two as compared to the embodiment shown in FIGS. 3-5, if the combined total number of turns in both coils 12 and 13 in FIG. 6 were to be kept the same as the number of turns in coil 12 shown in FIGS. 3-5.

Figure 7:
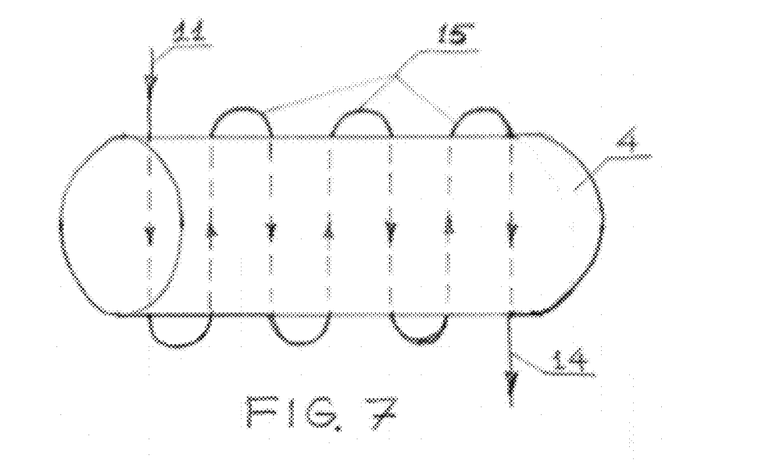
FIG. 7 is a schematic block diagram view of another cut fiber optic cable coil embodiment of the invention, showing a substantially sinusoidal aligned optical pathway.

Referring to the drawings, particularly to FIG. 7, which shows a schematic block diagram cross-sectional view of cuvette 4 in yet another embodiment of the invention, this embodiment, while similar to the embodiment shown in FIGS. 3-5 (especially FIG. 4), differs in that its cut fiber optic cable coil traverses cuvette 4 lengthwise instead of widthwise, forming a substantially sinusoidal optical pathway. It can be seen that after the light exits fiber optic cable 11 and goes through the sample in cuvette 4, it enters the first lower sinusoidal section of coil 15, exiting it and going through the sample again, entering the first upper sinusoidal section of coil 15, and so on, until it exits the last upper sinusoidal section of coil 15, goes through the sample in cuvette 4 for the last time, and enters fiber optic cable 14, proceeding to second polarizer 5 shown in FIG. 3.

Figure 8:
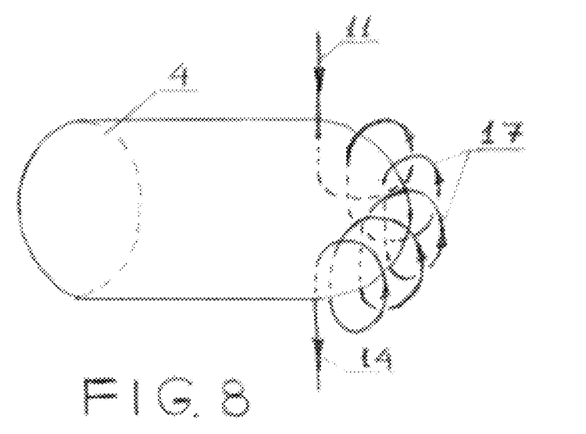
FIG. 8 is a schematic block diagram view of yet another cut fiber optic cable coil embodiment of the invention, showing a substantially poloidal aligned optical pathway.

Referring to the drawings, particularly to FIG. 8, which shows a schematic block diagram view of yet another fiber optic cable coil embodiment of the invention, which, while similar to the embodiment shown in FIGS. 3-5 (especially FIG. 4), differs in that its cut fiber optic cable coil 17 traverses cuvette 4 through a substantially poloidal optical pathway across cuvette 4, rather than along it. After the light exits fiber optic cable 11 and goes through the sample in cuvette 4, it enters the bottom of the first section of coil 17, going through the section, exiting it at the top of the section, going through the sample again, entering the bottom of the next section of coil 17, traversing it and exiting at the top, and so on, until it exits the top of the last section of coil 17, goes through the sample in cuvette 4 for the last time, and enters fiber optic cable 14, proceeding to second polarizer 5 shown in FIG. 3. It should be noted that FIGS. 2-8 are not drawn to scale, being just schematic representations.

To reach minimal intensity when there is human tissue in cuvette 4, second polarizer 5 has to be turned by that same angle $\alpha$, by which the flatly polarized light turned while passing through the sample in cuvette 4 in the embodiment shown in FIG. 2, or by a multiple of $\alpha$ in the embodiments shown in FIGS. 3-8. At each turn of polarizer 5 in the embodiment shown in FIG. 2, the intensity measuring circuitry of electronic module 8 records the turn angle corresponding to the minimal intensity. Thus, the turn angle $\alpha$ of the polarization plane of the light beam in a finger (or any other suitable part of a human body) is measured from about 1,000 up to about 5,000 times per minute in sync with the pulse for an embodiment shown in FIG. 2. The error of the calculated average value $\alpha$ in the embodiment shown in FIG. 2 was shown to be 7 to 10 times lower than in a single measurement of $\alpha$. Similarly, for the embodiments shown in FIGS. 3-8, the error is substantially lower than for a single measurement of $\alpha$, since the more turns in coil 12 of FIGS. 3-5, coils 12 and 13 of FIG. 6, coil 15 of FIG. 7, or coil 17 of FIG. 8, the greater the accuracy of the overall measurement. In all of the embodiments of the device shown in FIGS. 2-8, the zero-signal position of second polarizer 5 would have to be found prior to inserting a suitable body part, such as a finger or an earlobe, etc., into cuvette 4. In the embodiment shown in FIG. 2, the process of finding the zero-signal position is automated, whereas in the embodiments shown in FIGS. 3-8 this process may be realized in either a manual or an automatic manner, whereby in the manual version second polarizer 5 could be manually turned by means of a micrometer screw to find the zero-crossing.

The turn angle of the polarization plane of infrared light passing through a volume containing glucose is essentially proportional to the concentration of glucose as well as to the thickness of the tissue through which the IR beam is passing. If that thickness is kept constant, then the turn angle depends only on the concentration of glucose. This dependency would be proportional if the glucose were only present in the blood, but not in the skin, tissue layers under the skin, etc. Since glucose is present in a number of such layers, in which the concentration of glucose changes ever so slowly (months, if not years), the relationship between the concentration of glucose in blood and the turn angle is substantially linear.

Since the turn angle due to the polarization shift is very small (measured in minutes or fractions thereof rather than in degrees) and since it depends on cardiac activity (blood saturation of the tissue is higher during pulse maxima), as well as on blood pressure, it is not trivial to accurately correlate blood glucose concentration with the turn angle. It is necessary to account for various factors, including those listed above. Therefore, immediately prior to measuring blood glucose level, blood pressure is measured, which could be done either by means of an external third-party device or by a device incorporated into or connected to pulse sensor ring 16. If the measured pressure differs from the one at calibration, then the pressure difference (or the actual pressure) is entered into (or automatically transmitted to) the instant device, under the assumption that the k parameter in Equation (1) below is proportional to blood pressure.

The process of polarization plane turn angle $\alpha$ measurement is undertaken during the calibration of the device for a specific person A. Knowing angle $\alpha$, it is possible to determine the concentration of glucose $\phi$ in human blood, since these parameters are linearly dependent. The polarization plane turn angle could be described by the following equation:

$$\alpha = \alpha_A + k_A \phi \qquad (1)$$

where
   $\alpha$ is the polarization plane turn angle in a human finger (or any other part of the human body);

$\alpha_A$ is the polarization plane turn angle in the skin and hypodermic layers for person A, since they also contain glucose at quite stable concentration;

$\varphi$ is the concentration level of glucose in the human blood; and $k_A$ is a proportionality factor for person A.

During the process of calibration in a medical laboratory, it is necessary to obtain two readings (two data points), for example, before and after breakfast, thus necessitating drawing two blood samples at these different times. This gives us the following two readings for a given person A:

$$\left. \begin{array}{l} \alpha_1 = \alpha_A + k_A \varphi_1 \\ \alpha_2 = \alpha_A + k_A \varphi_2 \end{array} \right\} \quad (2)$$

where $\alpha_1$ is the measured polarization turn angle at first reading;

$\varphi_1$ is the measured blood glucose concentration at first reading;

$\alpha_2$ is the measured polarization turn angle at second reading; and $\varphi_2$ is the measured blood glucose concentration at second reading.

From this equation it's easy to determine parameters $\alpha_A$ and $k_A$ for a given person A:

$$\alpha_A = \frac{\alpha_1 \varphi_2 - \alpha_2 \varphi_1}{\varphi_2 - \varphi_1} \quad (3)$$

$$k_A = \frac{\alpha_2 - \alpha_1}{\varphi_2 - \varphi_1} \quad (4)$$

It follows from Equation (1) that the equation for calculating the concentration of glucose in the human blood is the following:

$$\varphi = \frac{\alpha - \alpha_A}{k_A} \quad (5)$$

where parameters $\alpha_A$ and $k_A$ are the calibration parameters for person A, which were determined by means of Equations (3) and (4), based on the measurements obtained via Equation (2) during calibration. For another person B these parameters shall be different: $\alpha_B$ and $k_B$, etc.

Values $\alpha_A$ and $k_A$ are entered or transmitted into the memory of the processor of the electronic module 8, with all the subsequent calculations based on Equation (5) made automatically during regular measurements, with blood sugar concentration shown on display 9. And since the device is microprocessor-based, these values could be entered into and stored in the device's memory for a reasonable number of measurements, for a reasonable time duration, and for a reasonable number of people, such as all family members; all the patients in the endocrinology department of a hospital; etc. Experience shows that these parameters hardly change for several months for any given person, and sometimes even up to a year, thereby enabling the recalibration process to be taken at half-year intervals or even less frequently for adults, and about every 2-3 months for children. Therefore, it would only take two finger pinpricks during the calibration process, and then the person would use the noninvasive device for about half a year until recalibration were required. The time period between calibrations may vary from person to person and may be determined experimentally, if desired.

One of the major problems in using the polarization effect of glucose is that blood vessels differ in thickness and the degree to which they get filled with blood. However, during the measurements of the turn angle of the polarization plane it was discovered that, in spite of various degrees of blood vessel saturation at different times, the results (points) are congregated near a certain value in sync with the heartbeat within a sufficiently broad pulse rate range. It is also known that the polarization angle turn is temperature-dependent; however, within the narrow temperature range of a live human body (typically, in the range between 36° C. and 40° C.), the variations in the turn angle are negligible and, if necessary, could be accounted for during calibration. Furthermore, the turn angle is proportional to the length of the pathway traversed by the light beam. Here, though, we assume it to be fixed, making the necessary adjustments during calibration, which should be quite obvious to one skilled in the art.

So as to "anchor" to a specific average blood vessel saturation (average amount of blood under the IR beam), second polarizer 5, which is located in the path of the IR beam, is rotated around its optical axis at approximately 1,000 to 5,000 rpm in the embodiment shown in FIG. 2. During the rotation, the maximum turn angle of the polarization plane is sampled (measured) by electronic means multiple times. Then the average turn angle of the polarization plane is calculated during one or several heartbeats and is substituted into Equation (5) above. Similarly, in the embodiments shown in FIGS. 3-8, the average turn angle is determined by dividing the sum total signal by the total number of turns in the fiber optic coil (or coils) plus one, mathematically expressed by the following formula:

$$\alpha_{avg} = \Sigma\alpha/(N+1) \quad (6)$$

where $\alpha_{avg}$ is the average turn angle of the polarization plane;

$\Sigma\alpha$ is the sum total signal obtained by adding up (N+1) polarization shift angles; and N is the number of turns in the coil, with the term "turn" applying also to each upper and lower semi-sinusoidal section of coil 15 in FIG. 7.

As numerous experiments have shown, in the specified waveband the absorption of IR radiation by human tissue is minimal, thus repeated shifting of polarization plane turn angle when passing IR beam through human tissue provides a good way of reducing the error of determination of blood glucose concentration. The confidence probability Y of attained results is 0.95 for a relative error of 3%.

The one or more heartbeats, during which the measurements and calculations take place, may be clocked by various means. In one embodiment, pulse sensor ring 16, which is placed on a person's finger, may incorporate a piezoelectric or optical sensor that detects the heartbeats, with one full heart cycle being the period between the two heartbeats. Since it is important to bypass the bone, which is not transparent to the IR, in one embodiment a finger grip (such as cuvette 4) allows a person to insert a finger until it comes to a full stop due to a fixed obstacle (such as the wall of the grip or cuvette 4). This enables us to know the location of the finger bone with a sufficient degree of accuracy, which, in turn, enables us to pass the laser beam through the 3 to 4 mm of flesh at the fingertip, as the fingernail presents no serious obstacle to the IR.

There could be other additional components present in the device, such as optical filters, focusing lenses, concentrators, collimators, mirrors, reflector arrays, prisms, etc., which should be obvious to one skilled in the art. It should also be noted that the disclosed embodiments are merely examples of how the underlying principles of the present invention may be implemented. There may be various other embodiments based on the same principles.

What is claimed is:

1. Optical polarization shift measuring system comprising:
   (A) a monochromatic optical source having a first linear polarizer;
   (B) substantially illuminated by the source, a sample stage capable of temporarily immobilizing a living sample;
   (C) proximate to the sample stage and within a predetermined angular range with respect to the source illumination of the sample, a narrow-band optical detector capable of detecting polarization angles from the illuminated sample; and
   (D) in conjunction with the source and the detector, a linear polarization angle comparator for comparing polarization of the source with a polarization maxima region measured by the detector; wherein the linear polarization angle comparator includes an electronic block having at least one item selected from the list: a synchronizer, a statistical data collector, a statistical data analyzer, and a statistical data processor; wherein the polarization maxima region is substantially a zero-signal crossing; and wherein the statistical data collector, the statistical data analyzer, and the statistical data processor are configured to collect, aggregate, and average measured data.

2. The system according to claim 1 wherein the optical source provides illumination in a predetermined region and the region is selected from the list:
   from about 0.75 μm to about 1.35 μm;
   from about 1.55 μm to about 1.85 μm; and
   from about 2.10 μm to about 2.30 μm.

3. The system according to claim 1 having a combination selected from the list:
   wherein the first linear polarizer is fixed and the detector includes a rotating front-end linear polarizer;
   wherein the first linear polarizer is fixed and the detector includes a rapidly rotating front-end linear polarizer;
   wherein the first linear polarizer is rotating and the detector includes a rapidly rotating front-end linear polarizer;
   wherein the first linear polarizer is rotating and the detector includes a rotating front-end linear polarizer;
   wherein the first linear polarizer is rotating and the detector includes a rapidly rotating front-end linear polarizer;
   wherein the first linear polarizer is rapidly rotating and the detector includes a fixed front-end linear polarizer;
   wherein the first linear polarizer is rapidly rotating and the detector includes a rotating front-end linear polarizer; and
   wherein the first linear polarizer is rapidly rotating and the detector includes a rapidly rotating front-end linear polarizer.

4. The system according to claim 1 wherein the sample stage is illuminated by the source via optical fiber.

5. The system according to claim 1 wherein the sample stage includes a cuvette.

6. The system according to claim 1 wherein the sample stage capable of temporarily immobilizing a living sample is configured to immobilize a living member selected from the list: a finger, a toe, an ear lobe, a roll of belly fat, a pinch of connective skin, and a pinch of fatty skin, wherein the living member being measured does not include a bone or wherein optical illumination does not pass through the bone of the living member being measured.

7. The system according to claim 1 wherein the sample stage includes a plurality of optical pathways traversing illumination between the optical source and the detector.

8. The system according to claim 7 wherein at least one of the optical pathways traversing the sample stage includes at least one optical element selected from the list: a concentrator, a lens, a collimator, a mirror, a reflector array, a prism, and a lenticular surface for projecting illumination from the source to the detector; or wherein at least one of the optical pathways traversing the sample stage includes at least one optical element selected from the list: a concentrator, a lens, a collimator, a mirror, a reflector array, a prism, and a lenticular surface for concentrating illumination from the source illuminated sample into the detector.

9. The system according to claim 1 wherein detector includes a front-end optical bandwidth filter.

10. The system according to claim 9 wherein the optical bandwidth filter allows light to pass through in a range selected from the list:
    from about 0.75 μm to about 1.35 μm;
    from about 1.55 μm to about 1.85 μm; and
    from about 2.10 μm to about 2.30 μm.

11. The system according to claim 1 wherein illumination traversing the sample further traverses via an optical fiber to the detector.

12. The system according to claim 1 further including external calibration of the sample having therein a substance selected from the list: at least one light polarization-shifting substance in the sample; glucose; a form of sugar; albumin; ascorbate; cholesterol; and a liquid crystal.

13. The system according to claim 1, further comprising a pulse sensor ring, which, in conjunction with the synchronizer, shifts the signal to substantially synchronize with blood pressure pulse maxima of the living sample in the sample stage, and synchronizes detecting the polarization angle with the pulse maxima of the living sample, wherein the pulse sensor ring includes an electronic block having at least one item selected from the list: a piezoelectric or optical sensor that detects the heartbeats, with one full heart cycle being the period between the two heartbeats.

14. A sample stage capable of temporarily immobilizing a living sample for use in an optical polarization shift measuring system and comprising a partially enclosed volume and a plurality of respectively aligned optical pathways through the volume, which are permitting traversing of predetermined illumination between an optical source and a detector comprising:
    (A) a monochromatic optical source having a first linear polarizer;
    (B) proximate to the sample stage and within a predetermined angular range with respect to the source illumination of the sample, a narrow-band optical detector capable of detecting polarization angles from the illuminated sample; and
    (C) in conjunction with the source and the detector, a linear polarization angle comparator for comparing polarization of the source with a polarization maxima region measured by the detector;
    (D) wherein the sample stage is comprising: a cuvette-like holder capable of temporarily immobilizing a living sample, wherein the at least one optical pathway permits traversing of predetermined illumination from the optical source, through the cuvette-like holder, and to the detector; and wherein the sample stage further includes a configuration selected from the list: at least one optical fiber to bring the illumination traversing a pathway of the plurality of pathways back into another pathway of the plurality of pathways;

wherein the at least one optical fiber and the plurality of optical pathways through the volume together form at least one substantially helictical pathway;

wherein the at least one optical fiber and the plurality of optical pathways through the volume together form at least one substantially sinusoidal pathway; and wherein the at least one optical fiber and the plurality of optical pathways through the volume together form at least one substantially poloidal pathway;

and further including at least one optical element selected from the list: a concentrator, a lens, a collimator, a mirror, a reflector array, a prism, and a lenticular surface for concentrating illumination over at least one pathway of the plurality of optical pathways through the volume.

15. The sample stage according to claim 14 further comprising a low-noise optical signal amplifier; wherein the plurality of optical pathways through the volume is from about 4 optical pathways to about 10 optical pathways; and wherein a pathway of the plurality of optical pathways through the volume includes not more than about a one-centimeter cross-section through the volume.

16. An article comprising a non-transitory tangible medium encoding computer-readable instructions that, when applied to one or more microprocessors, instruct one or more electronic components:
  (A) to illuminate a sample stage, having therein a temporarily immobilized living sample, with a monochromatic optical source having a first linear polarizer;
  (B) to detect polarization angle from the illuminated sample using a narrow-band optical detector proximate to the sample stage and within a predetermined angular range with respect to the source illumination of the sample; and
  (C) to compare the polarization of the source with a polarization maxima region measured by the detector by means of a statistical data collector, a statistical data analyzer, and a statistical data processor, wherein the statistical data collector, the statistical data analyzer, and the statistical data processor collect, aggregate, and average measured data.

17. The system according to claim 16, wherein the instructions include instructions that instruct the one or more microprocessors
  (A) to receive a time signal of blood pressure pulse maxima from a pulse sensor ring,
  (B) to shift the signal to substantially synchronize with a blood pressure pulse maxima of the living sample in the sample stage, and
  (C) to synchronize detecting the polarization angle with the pulse maxima of the living sample.

* * * * *